(12) United States Patent
Ghosh et al.

(10) Patent No.: US 6,936,638 B2
(45) Date of Patent: Aug. 30, 2005

(54) LIGANDS OF ADENINE NUCLEOTIDE TRANSLOCASE (ANT) AND COMPOSITIONS AND METHODS RELATED THERETO

(75) Inventors: Soumitra S. Ghosh, San Diego, CA (US); Yazhong Pei, San Diego, CA (US); Xiao-Qing Tang, San Diego, CA (US); Spiros J. Liras, Stonington, CT (US); Michael K. Ahlijanian, Mystic, CT (US)

(73) Assignees: Migenix Corp., San Diego, CA (US); Pfizer Inc., New York, NY (US)

( * ) Notice: Subject to any disclaimer, the term of this patent is extended or adjusted under 35 U.S.C. 154(b) by 45 days.

(21) Appl. No.: 10/741,595

(22) Filed: Dec. 19, 2003

(65) Prior Publication Data

US 2004/0192740 A1 Sep. 30, 2004

Related U.S. Application Data

(60) Provisional application No. 60/435,420, filed on Dec. 20, 2002.

(51) Int. Cl.$^7$ .................. A61K 31/19; C07D 313/04
(52) U.S. Cl. ................... 514/568; 549/471
(58) Field of Search ............. 514/568; 549/471

(56) References Cited

U.S. PATENT DOCUMENTS

| | | | | |
|---|---|---|---|---|
| 3,277,164 A | | 10/1966 | Haack et al. ........... 260/520 |
| 3,692,828 A | * | 9/1972 | Onopchenko et al. ..... 562/412 |
| 3,886,162 A | * | 5/1975 | Pfister et al. ........ 546/103 |
| 3,965,146 A | * | 6/1976 | Dahl .................. 560/59 |
| 4,683,244 A | * | 7/1987 | Moeller et al. ........ 514/568 |
| 4,935,240 A | * | 6/1990 | Nakai et al. .......... 424/400 |
| 4,980,372 A | * | 12/1990 | Nakai et al. .......... 514/510 |
| 5,217,994 A | | 6/1993 | Egbertson et al. ...... 514/484 |
| 5,426,196 A | | 6/1995 | Fang .................. 549/307 |
| 5,684,015 A | | 11/1997 | Mederski et al. ....... 514/303 |
| 5,888,941 A | | 3/1999 | Bartroli et al. ....... 504/262 |
| 5,990,133 A | | 11/1999 | Gaster et al. ......... 514/337 |
| 6,262,113 B1 | | 7/2001 | Widdowson et al. ...... 514/522 |
| 6,344,466 B2 | | 2/2002 | Soll et al. ........... 514/331 |
| 6,680,345 B2 | * | 1/2004 | Linz et al. ........... 514/643 |
| 6,855,341 B2 | * | 2/2005 | Smith ................. 424/642 |

FOREIGN PATENT DOCUMENTS

| | | |
|---|---|---|
| EP | 253666 A2 | 1/1988 |
| WO | WO 93/24442 | 12/1993 |
| WO | WO 99/36398 | 7/1999 |
| WO | WO 01/04087 | 1/2001 |
| WO | WO 03/080564 | 10/2003 |

OTHER PUBLICATIONS

US 6,274,628, 8/2001, Soll et al. (withdrawn)
Andreyev, A. Y. et al., "The ATP/ADP–antiporter is involved in the uncoupling effect of fatty acids on mitochondria," *European Journal of Biochemistry 182*: 585–592, 1989.
Beutner, G. et al., "Complexes between porin, hexokinase, mitochondrial creatine kinase and adenylate translocator display properties of the permeability transition pore. Implication for regulation of permeability transition by the kinases," *Bichimica et Biophysica Acta 1368*(1): 7–18, 1998.
Boveris and Chance, "The Mitochondrial Generation of Hydrogen Peroxide," *The Biochemical Journal 134*(3): 707–716, 1973.
Farrelly, E. et al., "A High–Throughput Assay for Mitochondrial Membrane Potential in Permeabilized Yeast Cells," *Analytical Biochemistry 293*(2): 269–276, Jun. 15, 2001.
Green and Reed, "Mitochondria and Apoptosis," *Science 281*:1309–1312, Aug. 28, 1998.
Korshunov, S.S. et al., "Fatty acids as natural uncouplers preventing generation of $O_2$ —and $H_2O_2$ by mitochondria in the resting state," *FEBS Letters 435*(2–3): 215–218, 1998.
Korshunov, S.S. et al., "High protonic potential actuates a mechanism of production of reactive oxygen species in mitochondria," *FEBS Letters 416*(1): 15–18, 1997.
Kroemer, G. et al., "The Mitochondrial Death/Life Regulator in Apoptosis and Necrosis," *Annual Review of Physiology 60*: 619–642, 1998.
Morin D. et al., "Mitochondria as target for antiischemic drugs," *Adv. Drug Deliv. Rev. 49*(1–2): 151–174, 2001.

(Continued)

*Primary Examiner*—Deborah C. Lambkin
(74) *Attorney, Agent, or Firm*—Seed IP Law Group PLLC

(57) ABSTRACT

Compounds which have utility in the treatment of conditions associated with altered mitochondrial function. The compounds have the following structure (I):

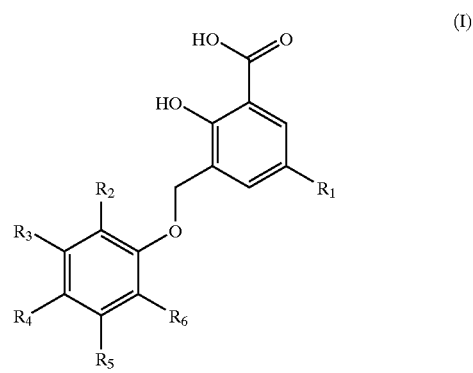

including stereoisomers, prodrugs, and pharmaceutically acceptable salts thereof, wherein $R_1$, $R_2$, $R_3$, $R_4$, $R_5$ and $R_6$ are as defined herein. Pharmaceutical compositions containing a compound of structure (I), as well as methods relating to the use thereof, are also disclosed.

20 Claims, No Drawings

OTHER PUBLICATIONS

Obatomi and Bach et al., "Inhibition of mitochondrial respiration and oxygen uptake in isolated rat renal tubular fragments by atractyloside," *Toxicology Letters* 89(2): 155–161, Dec. 16, 1996.

Skulachev, V.P., "Fatty acid circuit as a physiological mechanism of uncoupling of oxidative phosphorylation," *FEBS Letters* 294(3): 158–162, Dec. 1991.

Skulachev, V.P., "Why are mitochondria involved in apoptosis? Permeability transition pores and apoptosis as selective mechanisms to eliminate superoxide–producing mitochondria and cell," *FEBS Letters* 397(1): 7–10, 1996.

Wojtczak, L. et al., "Protonophoric Activity of Fatty Acid Analogs and Derivatives in the Inner Mitochondrial Membrane: A Further Argument for the Fatty Acid Cycling Model," *Archives of Biochemistry and Biophysics* 357(1): 76–84, Sep. 1, 1998.

Yu, X.X. et al., "Characteriztion of novel UCP5/BMCP1 isoforms and differential regulation of UCP4 and UCP5 expression through dietary or temperature manipulation," *The FASEB Journal* 14: 1611–1618, Aug. 2000.

Syamal and Singh, "Synthesis and Characterization of New Polymer Supported Chelating Resins," *Journal Polymer Mater.* 6: 175–179, 1989.

Tait, B.D. et al., "Catechol Based Inhibitors of 15–Lipoxygenase," *Bioorganic & Medicinal Chemistry Letters* 6(1): 93–96, 1996.

Tun , F. et al., "A Synthetic Approach Towards Homotrinuclear Complexes: Design of Mn(II), Cu(II) and Zn(II) Complexes Using a New Unsymmetrical Tetradenate Ligand," *Revue Roumaine de Chimie* 42(7): 579–585, 1997.

* cited by examiner

LIGANDS OF ADENINE NUCLEOTIDE TRANSLOCASE (ANT) AND COMPOSITIONS AND METHODS RELATED THERETO

CROSS-REFERENCE TO RELATED APPLICATION

This application claims the benefit of U.S. Provisional Patent Application No. 60/435,420 filed Dec. 20, 2002, where this provisional application is incorporated herein by reference in its entirety.

BACKGROUND OF THE INVENTION

1. Field of the Invention

The present invention relates generally to novel classes of compounds which interact with adenine nucleotide translocase (ANT), as well as to compositions and methods for using such compounds to treat conditions associated with altered mitochondrial function.

2. Description of the Related Art

Mitochondria are the main energy source in cells of higher organisms, and these organelles provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

Mitochondrial ultrastructural characterization reveals the presence of an outer mitochondrial membrane that serves as an interface between the organelle and the cytosol, a highly folded inner mitochondrial membrane that appears to form attachments to the outer membrane at multiple sites, and an intermembrane space between the two mitochondrial membranes. The subcompartment within the inner mitochondrial membrane is commonly referred to as the mitochondrial matrix. (For a review, see, e.g., Ernster et al., 1981 *J. Cell Biol.* 91:227s). The cristae, originally postulated to occur as infoldings of the inner mitochondrial membrane, have recently been characterized using three-dimensional electron tomography as also including tube-like conduits that may form networks, and that can be connected to the inner membrane by open, circular (30 nm diameter) junctions (Perkins et al., 1997, *Journal of Structural Biology* 119:260). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (>~10 kDa) molecules.

Altered or defective mitochondrial activity, including but not limited to failure at any step of the ETC, may result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (i.e., stroke).

In addition to free radical mediated tissue damage, there are at least two deleterious consequences of exposure to reactive free radicals arising from mitochondrial dysfunction that adversely impact the mitochondria themselves. First, free radical mediated damage may inactivate one or more of the myriad proteins of the ETC. Second, free radical mediated damage may result in catastrophic mitochondrial collapse that has been termed "permeability transition" (PT) or "mitochondrial permeability transition" (MPT). According to generally accepted theories of mitochondrial function, proper ETC respiratory activity requires maintenance of an electrochemical potential in the inner mitochondrial membrane by a coupled chemiosmotic mechanism, as described herein. Free radical oxidative activity, may dissipate this membrane potential, thereby preventing ATP biosynthesis and halting the production of a vital biochemical energy source. In addition, mitochondrial proteins such as cytochrome c may leak out of the mitochondria after MPT and may induce the genetically programmed cell suicide sequence known as apoptosis (Wilson, 1998 *Cell Death Differen.* 5:646–652) or programmed cell death (PCD).

Altered mitochondrial function characteristic of mitochondria associated diseases may also be related to loss of mitochondrial membrane electrochemical potential by mechanisms other than free radical oxidation, and MPT may result from direct calcium overload due to excitotoxic mechanisms or indirect effects of mitochondrial genes, gene products or related downstream mediator molecules and/or extramitochondrial genes, gene products or related downstream mediators, or from other known or unknown causes. Loss of mitochondrial electrochemical potential therefore may be a critical event in the progression of diseases associated with altered mitochondrial function, including degenerative diseases.

Mitochondrial defects, which may include defects related to the discrete mitochondrial genome that resides in mitochondrial DNA and/or to the extramitochondrial genome, which includes nuclear chromosomal DNA and other extramitochondrial DNA, may contribute significantly to the pathogenesis of diseases associated with altered mitochondrial function. For example, alterations in the structural and/or functional properties of mitochondrial components comprised of subunits encoded directly or indirectly by mitochondrial and/or extramitochondrial DNA, including alterations deriving from genetic and/or environmental factors or alterations derived from cellular compensatory mechanisms, may play a role in the pathogenesis of any disease associated with altered mitochondrial function. A number of diseases and conditions are thought to be caused by, or to be associated with, alterations in mitochondrial function. These include: Alzheimer's Disease (AD); diabetes mellitus; obesity; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD); myoclonic epilepsy ragged red fiber syndrome; osteoarthritis; and Friedrich's ataxia. The extensive list of additional diseases associated with altered mitochondrial function continues to expand as aberrant mitochondrial or mitonuclear activities are implicated in particular disease processes.

A hallmark pathology of AD and potentially other diseases associated with altered mitochondrial function is the death of selected cellular populations in particular affected tissues. Mitochondrial dysfunction is thought to be critical in the cascade of events leading to apoptosis (also referred to as "programmed cell death" or PCD) in various cell types (Kroemer et al., *FASEB J.* 9:1277–87, 1995), and may be a cause of apoptotic cell death in neurons of the AD brain. Altered mitochondrial physiology may be among the earliest events in PCD (Fiskum et al., *J. Cerebral Blood Flow and Met* 19:351–369, 1999; Murphy et al., *J. Cerebral Blood Flow and Met.* 19:231–245, 1999; Zamzami et al., *J. Exp. Med.* 182:367–77, 1995; Zamzami et al., *J. Exp. Med.* 181:1661–72, 1995) and elevated ROS levels that result from such altered mitochondrial function may initiate the apoptotic cascade (Ausserer et al., *Mol. Cell. Biol.* 14:5032–42,1994).

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al., *Biochim. Biophys. Act.* 1271:63, 1995). Localization of Bcl-2 to this membrane appears to be indispensable for modulation of apoptosis (Nguyen et al., *J. Biol. Chem.* 269: 16521–24, 1994). Thus, change in mitochondrial physiology may be important mediators of apoptosis.

Thus, in addition to their role in energy production in growing cells, mitochondria (or, at least, mitochondrial components) participate in cell death (eg., necrosis and apoptosis) (Newmeyer et al., 1994, *Cell* 79:353–364; Liu et al., 1996, *Cell* 86:147–157). Apoptosis is apparently also required for, inter alia, normal development of the nervous system and proper functioning of the immune system. Moreover, some disease states are thought to be associated with either insufficient (e.g., cancer, autoimmune diseases) or excessive (e.g., stroke damage, AD-associated neurodegeneration) levels of apoptosis. For general reviews of apoptosis, and the role of mitochondria therein, see Green and Reed (1998, *Science* 281:1309–1312), Green (1998, *Cell* 94:695–698) and Kromer (1997, *Nature Medicine* 3:614–620). Hence, agents that effect apoptotic events, including those associated with mitochondrial components, might have a variety of palliative, prophylactic and therapeutic uses.

The adenine nucleotide translocase (ANT), a nuclear encoded mitochondrial protein, is reportedly the most abundant protein of the inner mitochondrial membrane, forming dimers that comprise up to 10% of the total mitochondrial protein in highly oxidative tissue like cardiac and skeletal muscle. Three human ANT isoforms have been described that appear to differ in their tissue expression patterns, and other mammalian ANT homologues have been described. See, e.g., Wallace et al., 1998 in *Mitochondria & Free Radicals in Neurodegenerative Diseases,* Beal, Howell and Bodis-Wollner, Eds., Wiley-Liss, New York, pp. 283–307, and references cited therein. ANT proteins mediate the exchange across the mitochondrial inner membrane of ATP synthesized in the mitochondrial matrix for adenosine diphosphate (ADP) in the cytosol. This nucleotide exchange is the most active transport system in aerobic cells, and is a critical component in maintaining cellular energy metabolism (for a review see Klingenberg, *J. Bioenergetics and Biomembranes* 25:447–457, 1993). ANT has also been implicated as an important molecular component of the MPT pore, a $Ca^{2+}$-regulated inner membrane channel that plays an important modulating role in apoptotic processes.

By way of background, all five of the multisubunit complexes that mediate ETC activity are localized to the inner mitochondrial membrane. ANT represents the most abundant of the inner mitochondrial membrane proteins. In at least three distinct chemical reactions known to take place within the ETC, positively-charged protons are moved from the mitochondrial matrix, across the inner membrane, to the intermembrane space. This disequilibria of charged species creates an electrochemical potential of approximately 220 mV referred to as the "protonmotive force" (PMF), which is often represented by the notation $\Delta\psi$ and represents the sum of the electric potential and the pH differential across the inner mitochondrial membrane (see, e.g., Ernster et al., 1981 *J. Cell Biol.* 91:227s and references cited therein).

This membrane potential drives the ANT-mediated stoichiometric exchange of ATP and ADP across the inner mitochondrial membrane, and provides the energy contributed to the phosphate bond created when ADP is phosphorylated to yield ATP by ETC Complex V, a process that is "coupled" stoichiometrically with transport of a proton into the matrix. Under normal metabolic conditions, the inner membrane is impermeable to proton movement from the intermembrane space into the matrix, leaving ETC Complex V as the sole means whereby protons can return to the matrix. When, however, the integrity of the inner mitochondrial membrane is compromised, as occurs during MPT, which may accompany a disease associated with altered mitochondrial function, protons are able to bypass the conduit of Complex V without generating ATP, thereby "uncoupling" respiration because electron transfer and associated proton pumping yields no ATP. Thus, MPT involves the opening of a mitochondrial membrane "pore", a process by which, inter alia, the ETC and ATP synthesis are uncoupled, $\Delta\psi m$ collapses and mitochondrial membranes lose the ability to selectively regulate permeability to solutes both small (e.g., ionic $Ca^{2+}$, $Na^+$, $K^+$, $H^+$) and large (e.g., proteins) molecules.

Without wishing to be bound by theory, it is unresolved whether this pore is a physically discrete conduit that is formed in mitochondrial membranes, for example by assembly or aggregation of particular mitochondrial and/or cytosolic proteins and possibly other molecular species, or whether the opening of the "pore" may simply represent a general increase in the porosity of the mitochondrial membrane.

MPT may also be induced or blocked by compounds that bind one or more mitochondrial molecular components. Such compounds include, but are not limited to, atractyloside and bongkrekic acid, which are known to bind to ANT. Methods of determining appropriate amounts of such compounds to induce MPT are known in the art (see, e.g., Beutner et al., 1998 *Biochim. Biophys. Acta* 1368:7; Obatomi and Bach, 1996 *Toxicol. Lett.* 89:155; Green and Reed, 1998 *Science* 281:1309; Kroemer et al., 1998 *Annu. Rev. Physiol.* 60:619; and references cited therein). Thus, certain mitochondrial molecular components, such as ANT, may contribute to the MPT mechanism.

It is known that when fatty acids bind to ANT, they can induce what is termed "mild" mitochondrial uncoupling. In bioenergetic terms, the word "mild" means that the uncoupling is only evident at the resting state of the mitochondria (i.e. state 4, nonphosphorylating respiration) when the membrane potential is maximal, and that there is little or no effect during robust ATP production. Additionally, it has been discovered that this uncoupling induced by free fatty acids may be reversed by the addition of the ANT ligand carboxyatractyloside (see e.g., Andreyev et al., 1989 *Eur. J. Biochem.* 182:585–592; Skulachev, 1991 *FEBS Lett.* 294:158–162; Skulachev, 1996 *FEBS Lett.* 397:7–10; Korshunov et al., 1998 *FEBS Lett.* 435:215–218; Wojtczak et al., 1998 *Archives of Biochem. and BioPhys.* 357:76–84; and references cited therein), suggesting that carboxyatractyloside blocks the proton conductance induced by the free fatty acid. Since the high membrane potential in the resting state of the mitochondria potentiates mitochondrial free radical production (see e.g., Boveris and Chance, 1973 *Biochem. J.* 134:707–716; Korshunov et al., 1997 *FEBS Lett.* 416:15–18; and references cited therein), it has been theorized that periods of mild uncoupling may serve the purpose of reducing oxidative stress and could slow the rate of $Ca^{2+}$ uptake at high membrane potential (Skulachev, 1996 *FEBS Lett.* 397:7–10; Korshunov et al., 1997 *FEBS Lett.* 416:15–18; and references cited therein).

ANT proteins, as well as other transporter proteins known more generally as uncoupling proteins (UCPs), belong to a larger family of proteins known as the "carrier" family. The theory that mild uncoupling may be induced via brain-specific isoforms of UCPs has recently become the focus of several studies (Yu et al., 2000 *FASEB J.* 14(11):1611–1618; Farrelly et al., 2001 *Analytical Biochem.* 293:269–276; and references cited therein). Additionally, mild mitochondrial uncoupling has recently been proposed as a possible treatment for ischemia-reperfusion injury (Morin et al., 2001 *Advanced Drug Delivery Rev.* 49:151–174; and references cited therein).

Clearly there is a need for compounds and methods that limit or prevent damage to organelles, cells and tissues that may directly or indirectly result from alterations in mitochondrial function including mitochondrial dysfunction, such as mitochondrial permeability transition that is the cause or consequence of oxidative phosphorylation uncoupling and/or intracellular free radical generation. Accordingly, while significant advances have been made in this field, there is still a need in the art for small molecules that will bind, form a complex with, or otherwise interact with ANT. There is also a need for pharmaceutical compositions containing the same, as well as methods relating to the use thereof to treat conditions associated with altered mitochondrial function. The present invention fulfills these needs and provides other related advantages.

BRIEF SUMMARY OF THE INVENTION

This invention is directed to novel classes of compounds which bind, form a complex with, or otherwise interact with ANT. This invention is also directed to compositions containing one or more of such compounds in combination with one or more pharmaceutically acceptable carriers, as well as to methods for treating or preventing conditions associated with altered mitochondrial function with such compounds. Without wishing to be bound by theory, it is believed that the compounds of the present invention interact with ANT to induce mild mitochondrial uncoupling.

In one embodiment, this invention is directed to compounds which have the following structure (I):

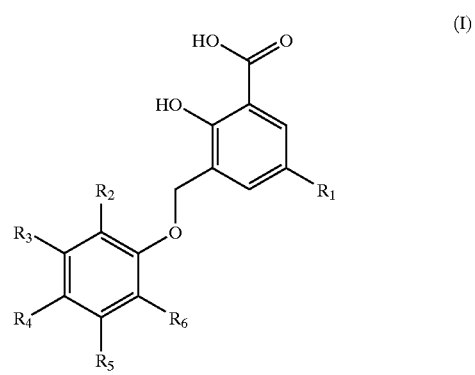

(I)

including stereoisomers, prodrugs, and pharmaceutically acceptable salts thereof, wherein $R_1$, $R_2$, $R_3$, $R_4$, $R_5$ and $R_6$ are as defined herein.

In addition, compositions containing a compound of this invention in combination with a pharmaceutically acceptable carrier are disclosed. Methods of use for treating or preventing conditions associated with altered mitochondrial function, the treatment or prevention of which may be effected or facilitated by inducing mild mitochondrial uncoupling, with the compounds of this invention and compositions comprising them are also disclosed. In particular, methods of use for the treatment and prevention of Alzheimer's Disease, diabetes mellitus, obesity, Parkinson's Disease, Huntington's disease, dystonia, Leber's hereditary optic neuropathy, schizophrenia, mitochondrial encephalopathy, lactic acidosis, and stroke (MELAS), cancer, psoriasis, hyperproliferative disorders, mitochondrial diabetes and deafness (MIDD), myoclonic epilepsy ragged red fiber syndrome, osteoarthritis and Friedrich's ataxia, as well as other conditions associated with altered mitochbndrial function with the compounds of this invention and compositions comprising them are disclosed.

These and other aspects of the present invention will become evident upon reference to the following detailed description and attached drawings. In addition, various references are set forth herein which describe in more detail certain aspects of this invention, and are incorporated by reference in their entireties

DETAILED DESCRIPTION OF THE INVENTION

In one embodiment of the present invention, compounds are disclosed having the following structure (I):

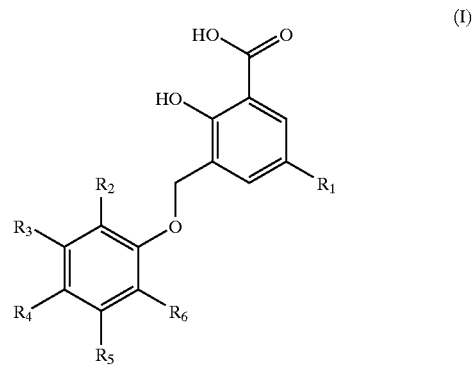

(I)

or a stereoisomer, prodrug or pharmaceutically acceptable salt thereof, wherein:

$R_1$ is hydrogen, halogen, nitro, cyano, alkyl, substituted alkyl, alkoxy, hydroxy, aryl, substituted aryl, —NHC(=O)R', heteroaryl or substituted heteroaryl;

$R_2$, $R_3$, $R_5$ and $R_6$ are the same or different and independently hydrogen, halogen, nitro, cyano, alkyl, substituted alkyl, alkoxy, hydroxy, aryl, substituted aryl, heteroaryl or substituted heteroaryl;

$R_4$ is hydrogen, halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, —O—$R_7$, —C(=O)—$R_7$, —C(=O)O—$R_7$, —C(=O)—NH—$R_7$ or —NHC(=O)R";

$R_7$ is hydrogen, alkyl, substituted alkyl, aryl, substituted aryl, arylalkyl or substituted arylalkyl;

R' and R" are the same or different and independently alkyl, substituted alkyl, aryl, substituted aryl, heteroaryl or substituted heteroaryl; and $R_4$ and $R_5$ or $R_5$ and $R_6$, taken together with the carbon atoms to which they are attached, optionally form a substituted or unsubstituted homocycle.

As used herein, the above terms have the meanings set forth below.

"Alkyl" means a straight chain or branched, noncyclic or cyclic, unsaturated or saturated aliphatic hydrocarbon containing from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, —CH₂cyclohexyl, and the like; while unsaturated cyclic alkyls include cyclopentenyl, cyclohexenyl, —CH₂cyclohexenyl, and the like.

"Aryl" means an aromatic carbocyclic moiety such as phenyl or naphthyl (i.e., 1- or 2-naphthyl).

"Arylalkyl" means an alkyl having at least one alkyl hydrogen atom replaced with an aryl moiety, such as benzyl, —(CH₂)₂phenyl, —(CH₂)₃phenyl, and the like.

"Heteroaryl" means an aromatic heterocycle ring of 5 to 10 members and having at least one heteroatom selected from nitrogen, oxygen and sulfur, and containing at least 1 carbon atom, including both mono- and bi-cyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —(CH₂)₂pyridyl, —(CH₂)₃pyridyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Homocycle" means a saturated, unsaturated or aromatic carbocyclic moiety.

The term "substituted" as used herein means any of the above groups (i.e., alkyl, aryl, arylalkyl, heteroaryl heteroarylalkyl, heterocycle and homocycle) wherein at least one hydrogen atom is replaced with a substituent. In the case of an oxo substituent ("=O"), two hydrogen atoms are replaced. When substituted, "substituents" within the context of this invention include oxo, halogen, hydroxy, cyano, nitro, amino, alkylamino, dialkylamino, alkyl, substituted alkyl, alkoxy, thioalkyl, sulfonylalkyl, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, homocycle, substituted homocycle, —NR$_a$R$_b$, —NR$_a$C(=O)R$_b$, —NR$_a$C(=O)NR$_a$NR$_b$, —NR$_a$C(=O)OR$_b$, —NR$_a$SO₂R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)₂R$_a$, —OS(=O)₂R$_a$, —S(=O)₂OR$_a$, —CH₂S(=O)₂R$_a$, —CH₂S(=O)₂N(R$_a$)₂, =NS(=O)₂R$_a$, and —S(=O)₂N(R$_a$)₂, wherein R$_a$ and R$_b$ are the same or different and independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, homocycle or substituted homocycle.

"Alkoxy" means an alkyl moiety attached through an oxygen bridge (i.e., —O-alkyl) such as methoxy, ethoxy, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Haloalkyl" means an alkyl moiety having at least one alkyl hydrogen replaced with halogen, such as —CF₃, and the like.

"Halogen" means fluoro, chloro, bromo and iodo.

"Sulfonylalkyl" means an alkyl moiety attached through a sulfonyl bridge (i.e., —SO₂-alkyl) such as methylsulfonyl, ethylsulfonyl, and the like.

"Thioalkyl" means an alkyl moiety attached through a sulfur bridge (i.e., —S-alkyl) such as methylthio, ethylthio, and the like.

Compounds of this invention include embodiments of structure (I) wherein $R_1$ is hydrogen or alkyl. In more specific embodiments, alkyl is methyl or —C(CH₃)₂—CH₂—C(CH₃)₂—CH₃.

Compounds of this invention also include embodiments of structure (I) wherein $R_2$ is hydrogen.

Compounds of this invention also include embodiments of structure (I) wherein $R_3$ is hydrogen.

Compounds of this invention also include embodiments of structure (I) wherein $R_4$ is hydrogen, halogen, alkyl or heteroaryl. In more specific embodiments, alkyl is tert-butyl and heteroaryl is thiophenyl.

Compounds of this invention also include embodiments of structure (I) wherein $R_5$ is hydrogen or halogen.

Compounds of this invention also include embodiments of structure (I) wherein $R_6$ is hydrogen or halogen.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts include those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the patent compound. Prodrugs include, for example, compounds of this invention wherein hydroxy or amine groups are bonded to any group that, when administered to a patient, cleaves to form the hydroxy or amine groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of the present invention may be prepared by known organic synthesis techniques, including the methods described in more detail in the Examples.

Activities of the compounds of the present invention are typically calculated from the $IC_{50}$ as the concentration of a compound necessary to displace 50% of a detectable (i.e., detectably labeled, for example, radiolabeled) ligand from ANT molecules, which may be present as isolated or purified polypeptides or as components of preparations containing isolated mitochondria or submitochondrial particles (SMP) using established ligand binding assays or modifications thereof. For example, compounds may be tested for their ability to compete with radiolabeled atractyloside (ATR), or with a radiolabeled ATR derivative, for binding to isolated ANT polypeptides or to ANT present in isolated mitochondria or SMP.

As another example, the relative affinities for ANT of various compounds of the present invention may be determined by a fluorescence assay that exploits the fluorescent properties of an ATR derivative. When such an ATR derivative is bound to ANT, the fluorescence is quenched. When, however, such an ATR derivative is displaced from ANT by a known concentration of ATR or an ATR derivative that is an ANT ligand, fluorescence dequenching that results from displacement of the fluorophore can be measured in real time.

Briefly, a mitochondrial preparation is washed and resuspended in a suitable buffer in the presence of an ATR derivative with fluorescent properties, washed to remove unbound fluorophore and placed in a fluorometer equipped with a light source and filter set appropriate for the fluorophore. Fluorescence intensity is monitored as a function of time, and a candidate compound is then added to determine its ability to compete with the ATR derivative for binding to ANT, as evidenced by a change in detectable relative fluorescence intensity units. After the fluorescence signal has stabilized, any additional ATR derivative that remains bound to ANT is displaced by adding an excess (e.g., $\mu$M quantities) of ATR as a competitive inhibitor, to determine maximal signal intensity and therefrom calculate the proportion of the ATR derivative displaced by the candidate compound. Those having familiarity with the art will appreciate that variations and modifications may be made to ANT-binding assays such as those illustrated above and described in the Examples for determining the activities and $IC_{50}$ values of candidate compounds, and which are not intended to be limiting. See also U.S. Ser. No. 09/569,327 entitled "Production of Adenine Nucleotide Translocator (ANT), Novel ANT Ligands and Screening Assays Therefor", which is hereby incorporated by reference.

As mentioned above, it is believed that the compounds of this invention bind, form a complex with, or otherwise interact with ANT to induce mild mitochondrial uncoupling, and are thereby useful in the treatment of a variety of conditions associated with altered mitochondrial function. In this regard, the compounds of this invention have utility over a broad range of therapeutic applications, and may be used to treat conditions including (but not limited to) Alzheimer's Disease, diabetes mellitus, obesity, Parkinson's Disease, Huntington's disease, dystonia, Leber's hereditary optic neuropathy, schizophrenia, mitochondrial encephalopathy, lactic acidosis, and stroke (MELAS), cancer, psoriasis, hyperproliferative disorders, mitochondrial diabetes and deafness (MIDD), myoclonic epilepsy ragged red fiber syndrome, osteoarthritis and Friedrich's ataxia.

The compounds of the present invention are preferably part of a pharmaceutical composition when used in the methods of the present invention. The pharmaceutical composition will include at least one of a pharmaceutically acceptable carrier, dilutent or excipient, in addition to a therapeutically effective amount of one or more compounds of the present invention and, optionally, other components.

The "therapeutically effective amount" of a compound of the present invention will depend on the route of administration, the type of warm-blooded mammal being treated, and the physical characteristics of the specific mammal under consideration. These factors and their relationship to determining this amount are well known to skilled practitioners in the medical arts. Furthermore, this amount and the method of administration can be tailored to achieve optimal efficacy but will depend on such factors as weight, diet, concurrent medication and other factors which as noted those skilled in the medical arts will recognize. Typically, dosages will be between about 0.01 mg/kg and 100 mg/kg body weight, preferably between about 0.01 and 10 mg/kg body weight.

"Pharmaceutically acceptable carriers" for therapeutic use are well known in the pharmaceutical art. For compositions formulated as liquid solutions, acceptable carriers and/or diluents include saline and sterile water, and may optionally include antioxidants, buffers, bacteriostats and other common additives. Preservatives, stabilizers, dyes and even flavoring agents may also be provided in the pharmaceutical composition. The compositions can also be formulated as pills, capsules, granules, or tablets that contain, in addition to a compound of this invention, dispersing and surface active agents, binders, and lubricants. One skilled in this art may further formulate a compound in an appropriate manner, and in accordance with accepted practices, such as those disclosed in *Remington's Pharmaceutical Sciences*, Gennera, Ed., Mack Publishing Co., Easton, Pa. 1990.

The pharmaceutical compositions that contain one or more compounds that interact with ANT may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

EXAMPLES

The following Examples are offered for purposes of illustration, not limitation. Those skilled in the art will recognize, or be able to ascertain through routine experimentation, numerous equivalents to the specific substances and procedures described herein. Such equivalents are considered to be within the scope of the present invention.

TABLE 1

| Abbreviations used in Examples | |
|---|---|
| Reagents: | |
| AcCl | acetyl chloride |
| DIEA | diisopropylethylamine |
| DMAP | 4-N,N,-dimethylaminopyridine |
| Et$_3$N | triethyl amine |
| TFA | trifluoroacetic acid |
| Solvents: | |
| DCM | dichloromethane |
| DMF | dimethylformamide |
| DMSO | dimethylsulfoxide |
| EtOAc | ethyl acetate |

TABLE 1-continued

| Abbreviations used in Examples | |
|---|---|
| MeOH | methanol |
| THF | tetrahydrofuran |
| Others: | |
| rt | room temperature |
| g | gram |
| hr | hour |
| min | minute |

Example 1

Synthesis of Representative Compounds

These examples illustrate the preparation of certain representative compounds.

A. General Synthesis of 3-Aryloxymethyl Analogs of Salicylic Acid

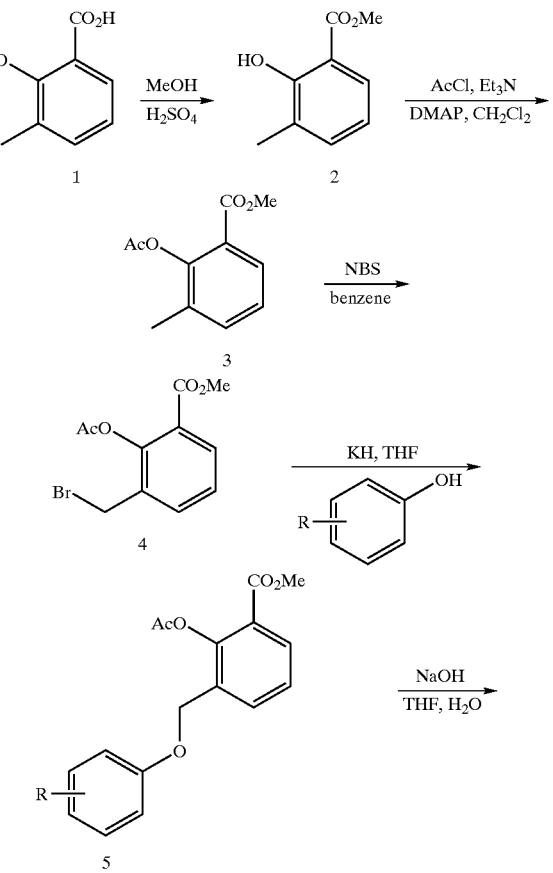

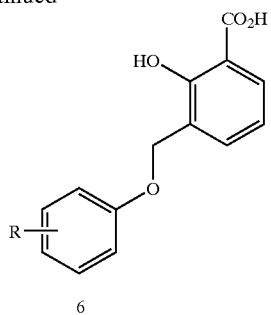

6

Synthesis of 3-methylsalicyclic acid methyl ester, structure 2:

A mixture of 3-methylsalicyclic acid 1 (15.2 g, 100 mmol), MeOH (300 mL), and concentrated $H_2SO_4$ (40 mL) was refluxed overnight. The excess amount of MeOH was evaporated under reduced pressure, and then the residue was diluted carefully with $H_2O$ and extracted with EtOAc twice. The combined organic layer was washed with saturated $NaHCO_3$, brine, and dried over $Na_2SO_4$, filtered, concentrated, and the residue was purified by column chromatography on silica gel (EtOAc/hexane: 5/95) to give structure 2 (13.8 g, 83%) as a colorless oil.

Synthesis of Structure 3:

To a solution of DMAP (561 mg, 4.59 mmol), $Et_3N$ (12.8 mL, 91.8 mmol) and AcCl (5.41 g, 68.9 mmol) in $CH_2Cl_2$ (150 mL) was added structure 2 (7.62 g, 45.9 mmol) in $CH_2Cl_2$ at 0° C. under argon. The mixture was then stirred at room temperature overnight, diluted with EtOAc, washed with saturated $NaHCO_3$, brine, and dried over $Na_2SO_4$, filtered, concentrated, and the residue was purified by column chromatography on silica gel (EtOAc/hexane: 10/90) to give structure 3 (9.18 g, 96%) as a white solid.

Synthesis of Structure 4:

A solution of structure 3 (5.74 g, 27.6 mmol), NBS (6.39 g, 35.9 mmol), and 1,1'-azobis(cyclohexanecarbonitrile) (337 mg, 1.38 mmol) in benzene (100 mL) was gently refluxed overnight. The reaction mixture was then cooled down to room temperature, and the precipitate was filtered off. The filtrate was concentrated under reduced pressure, and the residue was purified by column chromatography on silica gel (EtOAc/hexane: 10/90) to give structure 4 (6.74 g, 85%) as a white solid. $^1$H NMR (500 MHz, $CDCl_3$) δ 2.42 (s, 3H), 3.88 (s, 3H), 4.44 (s, 2H), 7.30 (t, J=7.8 Hz, 1H), 7.63 (d, =7.8 Hz, 1H), 7.99 (d, =7.8 Hz, 1H).

Synthesis of Structure 5 (R=4-amyl):

To a stirred suspension of KH (147 mg, 30% suspension in mineral oil, 1.1 mmol) in dry THF (5 mL) was added 4-amylphenol (164 mg, 1.0 mmol) at 0° C. under argon. After stirring at that temperature for half an hour, a solution of structure 4 (317 mg, 1.1 mmol) in dry THF was added dropwise. The mixture was then stirred at 0° C. and allowed to warm to room temperature overnight. The reaction was carefully quenched with saturated $NaHCO_3$, and extracted twice with EtOAc. The combined organic layer was washed with brine, and dried over $Na_2SO_4$, filtered, concentrated, and the residue was purified by column chromatography on silica gel (EtOAc/hexane: 5/95) to give structure 5 (R=4-amyl) (161 mg, 49%) as a colorless oil. $^1$H NMR (500 MHz, $CDCl_3$) δ 0.68 (t, J=7.3 Hz, 3H), 1.26 (s, 6H), 1.61 (q, J=7.3 Hz, 2H), 3.96 (s, 3H), 5.15 (s, 2H), 6.90–6.95 (m, 3H), 7.24 (d, J=9.1 Hz, 2H), 7.68 (d, J=7.6 Hz, 1H), 7.82 (d, J=7.6 Hz, 1H); MS (calculated for $C_{20}H_{25}O_5$) 329.17 $[M+H]^+$, found 329.0.

Synthesis of Structure 6 (R=4-amyl):

A stirred solution of structure 5 (62 mg, 0.19 mmol) and NaOH (3 M, 0.32 mL) in $THF/H_2O$ (10:1, 5 mL) was refluxed overnight. After it was cooled down to rt, the reaction mixture was acidified with 1 M HCl, extracted with $CH_2Cl_2$, washed with brine, and dried over $Na_2SO_4$, filtered, concentrated, and the residue was recrystallized from EtOAc and hexane to give structure 6 (R=4-amyl) (36 mg, 61%) as a white solid. $^1$H NMR (500 MHz, DMSO-$d_6$) δ 0.70 (t, J=7.2 Hz, 3H), 1.28 (s, 6H), 1.62 (q, J=7.2 Hz, 2H), 4.65 (s, 2H), 6.89–6.96 (m, 3H), 7.26 (d, J=7.8 Hz, 2H), 7.71 (d, J=7.7 Hz, 1H), 7.85 (d, J=7.7 Hz, 1H), 11.42 (s, 1H); MS (calculated for $C_{19}H_{21}O_3$) 297.14 $[M+H^+—H_2O]$, found 297.1.

B. General Synthesis of 3-Aryloxymethyl Analogs of 5-Alkyl Salicyclic Acid

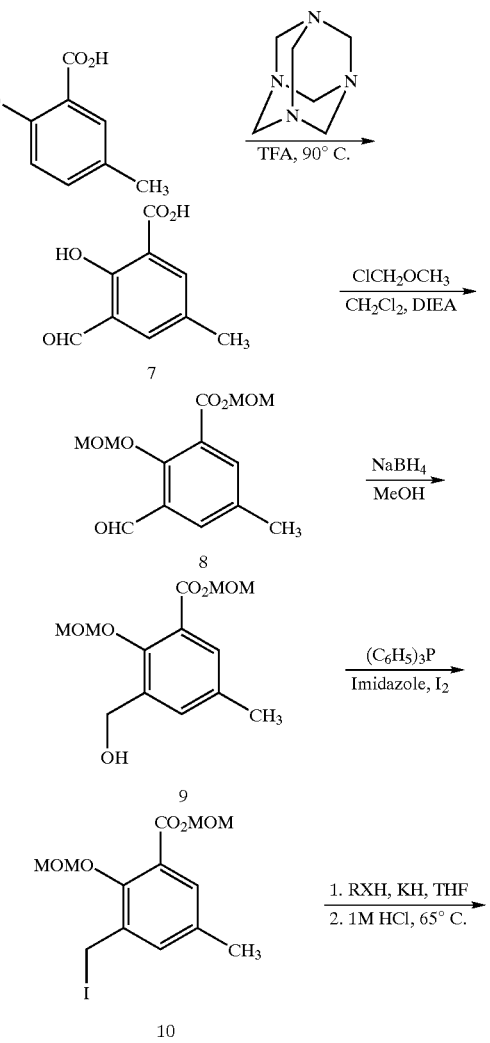

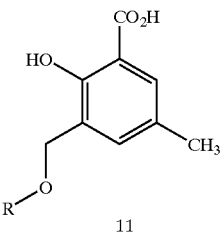

11

Synthesis of Structure 7 (Ruell et al., *J. Org. Chem.* 64:5858–5866, 1999):

A solution of 5-methylsalicylic acid (5 g, 33 mmol) and hexamethylenetetramine (22 g, 150 mmol) in TFA was warmed to 90° C. and stirred for 14 hrs. The orange solution that resulted was poured into dilute hydrochloric acid (1 M, 500 mL) and the solution was stirred for a further 6 hrs. The white precipitate that resulted was filtered and then dried in a vacuum desiccator for 2 days. Structure 7 (6.7 g) was obtained as a damp off-white solid.

Synthesis of Structure 8:

To a stirred solution of structure 7 (3.0 g, 16.6 mmol) dissolved in dichloromethane (140 mL) was added diisopropylethylamine (7.2 mL, 41.6 mmol). The solution was cooled to 0C and chloromethyl methyl ether (2.8 mL, 36.9 mmol) was added drop-wise. After 30 min, the reaction mixture was warmed to room temperature and stirred for an additional 1 hr. A saturated solution of sodium bicarbonate (50 mL) was added and the mixture was vigorously stirred for 10 min. The organic phase was removed and the aqueous phase was extracted with dichloromethane (20 mL). The combined organic phase was dried over sodium sulfate, filtered and evaporated to give structure 8 (2.47 g, 55% yield) as a yellow oil. $R_f$ [40-60 petroleum ether:ethyl acetate (4:1)]=0.48; $^1$H NMR (400 MHz, CDCl$_3$) δ 2.41 (s, 3H), 3.56 (s, 3H), 3.57 (s, 3H), 5.17 (s, 2H), 5.48 (s, 2H), 7.85 (d, J=2.0 Hz, 1H), 7.95 (d, J=2.0 Hz, 1H), 10.41 (s, 1H); $^{13}$C NMR (100 MHz, CDCl$_3$) δ 20.5, 58.0, 91.3, 102.4, 124.8, 130.9, 132.6, 134.4, 137.9, 158.5, 164.4, 199.1; LC/MS 269.4 [M+H]$^+$, 286.1 [M+NH$_4$]$^+$, 554.4 [2M+NH$_4$]$^+$.

Synthesis of Structure 9:

To a solution of structure 8 (2.45 g, 9.1 mmol) in methanol (50 mL) at 0° C. was added sodium borohydride (0.50 g, 13 mmol). The solution was warmed to room temperature and stirring was continued for 30 min. The reaction mixture was diluted with brine (250 mL) and extracted with ethyl acetate (3×100 mL). The combined organic phase was dried over sodium sulfate, filtered and evaporated to give structure 9 (2.32 g, 94% yield) as a colorless oil. $R_f$ [40-60 petroleum ether:ethyl acetate (4:1)]=0.21; $^1$H NMR (400 MHz, CDCl$_3$) δ 2.28 (s, 3H), 3.31 (brs, 1H), 3.48 (s, 3H), 3.54 (s, 3H), 4.55 (d, J=6.0 Hz, 2H), 5.02 (s, 2H), 5.38 (s, 2H), 7.32 (d, J=2.0 Hz, 1H), 7.61 (d, J=2.0 Hz, 1H); $^{13}$C NMR (100 MHz, CDCl$_3$) δ 20.6, 57.4, 57.8, 60.8, 91.0, 101.5, 123.4, 131.7, 134.3, 135.6, 136.1, 154.8, 165.0; LC/MS 271.3 [M+H]$^+$, 558.4 [2M+NH$_4$]$^+$.

Synthesis of Structure 10:

To a stirred solution of triphenylphosphine (728 mg, 2.77 mmol) in dichloromethane (5.0 mL) at room temperature was added imidazole (189 mg, 2.77 mmol) and iodine (704 mg, 2.77 mmol), followed by a solution of structure 9 (500 mg, 1.85 mmol) dissolved in dichloromethane (2.0 mL) and stirring was continued for 1 hr. The reaction mixture was loaded directly onto silica and eluted with 40-60 petroleum ether:ethyl acetate (6:1) to give structure 10 (450 mg,, 64% yield) as a colorless oil. $R_f$ [40-60 petroleum ether:ethyl acetate (4:1)]=0.60; $^1$H NMR (400 MHz, CDCl$_3$) δ 2.32 (s, 3H), 3.55 (s, 3H), 3.63 (s, 3H), 4.56 (s, 2H), 5.15 (s, 2H), 5.44 (s, 2H), 7.38 (d, J=2.0 Hz, 1H), 7.59 (d, J=2.0 Hz, 1H); $^{13}$C NMR (100 MHz, CDCl$_3$) δ −0.2, 20.5, 57.7, 57.9, 91.1, 101.1, 124.6, 131.9, 134.1, 134.2, 135.6, 153.6, 165.0; LC/MS 381.0 [M+H]$^+$, 398.4 [M+NH$_4$]$^+$, 778.0 [2M+NH$_4$]$^+$.

Synthesis of Structure 11 (R=3-bromophenyl):

To a vigorously stirred solution of potassium hydride (4.2 mg, 105 μmol) in THF (0.5 mL) under a nitrogen atmosphere at 0° C. was added 3-bromophenol (16.3 mg, 94.2 μmol). Stirring was continued for 10 min at 0° C. and then structure 10 (35.8 mg, 94.2 μmol) in THF (0.5 mL) was added. The reaction mixture was placed in a cold room (−10° C.) overnight (14 hrs). The reaction mixture was then diluted with brine (2 mL) and extracted with dichloromethane (2×3 mL). The combined organic phase was dried with sodium sulfate, filtered and evaporated under a stream of nitrogen. The resultant oil was dissolved in acetonitrile:water:concentrated HCl (90:9:1) and heated to 65° C. for 3 hrs. The reaction mixture was then frozen and lyophilized to give structure 11 (R=3-bromophenyl (29.8 mg, 94% yield) as an off white powder. $^1$H NMR (400 MHz, CDCl$_3$/CD$_3$OD) δ 2.25 (s, 3H), 5.04 (s, 2H), 6.86–6.89 (m, 1H), 7.01–7.13 (m, 3H), 7.44 (d, J=1.6 Hz, 1H), 7.63 (d, J=1.6 Hz, 1H), 10.50 (s, 1H).

C. General Synthesis of 3-Aryloxymethyl Analogs of 5-Aryl Salicyclic Acid

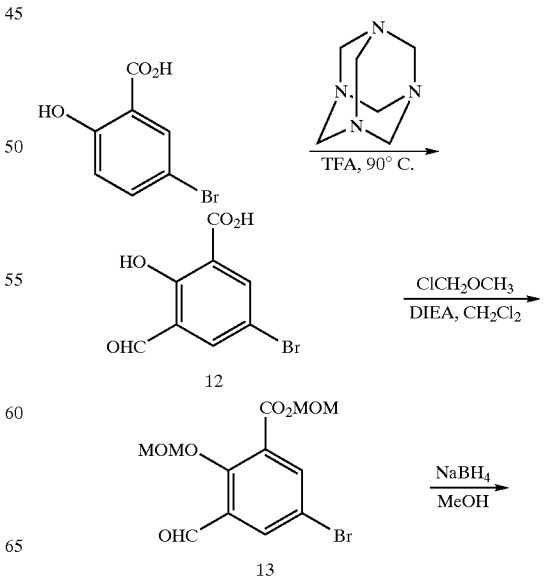

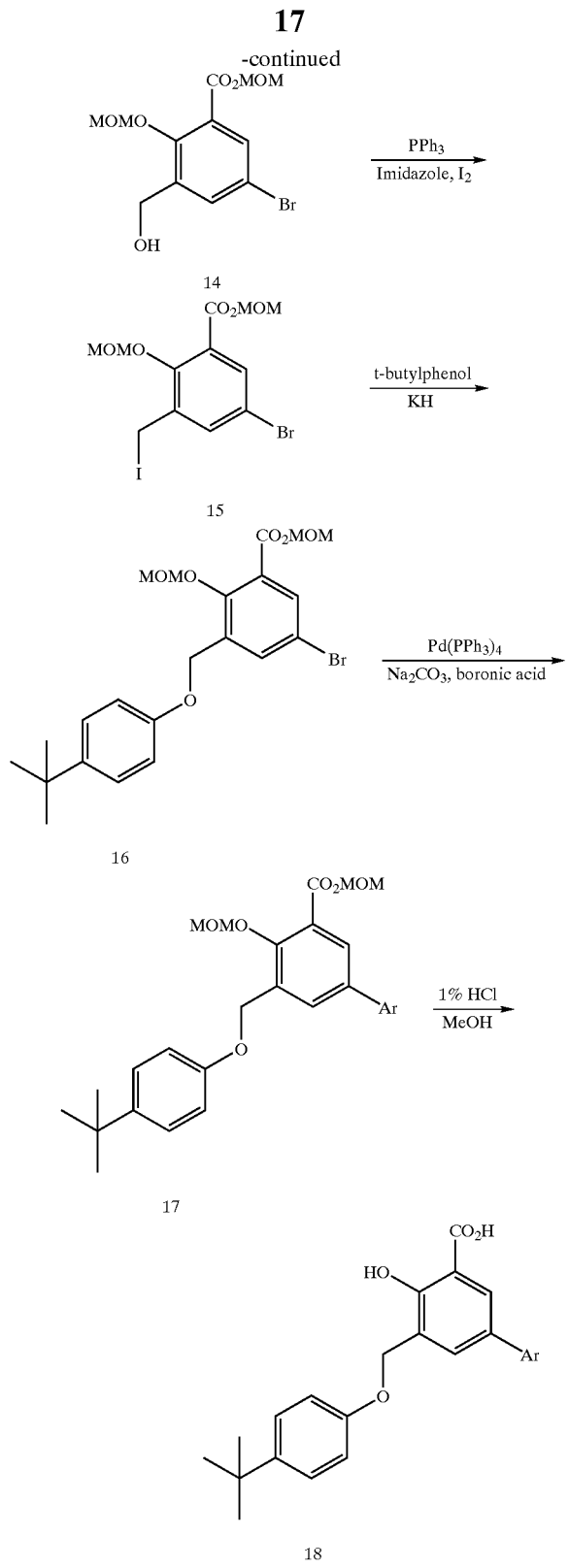

for 6 hrs and the resulting white precipitate filtered. The precipitate was recrystallized from ethanol:water and dried in vaccuo to give structure 12 (4.7 g, 64% yield) as a white solid. $^1$H NMR (400 MHz, $d_6$-DMSO) δ 7.99 (d, J=2.75 Hz, 1H), 8.18 (d, J=2.56 Hz, 1H), 10.35 (s, 1H); HPLC (214 nm) $t_R$=6.98 (95.9%) min; LC/MS 245.3 [M+H]$^+$, 490.9 [2M+H]$^+$.

Synthesis of Structure 13:

Structure 12 (2.0 g, 8.1 mmol) was dissolved in DCM (100 mL) and DIEA (4.0 mL, 24.3 mmol) was added. The reaction mixture was cooled to 0° C. and chloromethyl methyl ether (1.35 mL, 17.8 mmol) was added. The reaction was warmed to room temperature and stirred for 1 hr. Saturated NaHCO$_3$ (30 mL) was added and the mixture was stirred for a further 20 min. The organic phase was removed and the aqueous phase was extracted with further DCM (30 mL). The combined organic phase was dried with Na$_2$SO$_4$, filtered and evaporated to give structure 13 (3.88 g) as a brown oil (containing some residual water). $^1$H NMR (400 MHz, CDCl$_3$) δ 3.56 (s, 3H), 3.57 (s, 3H), 5.19 (s, 2H), 5.48(s, 2H), 8.13 (d, J=2.75 Hz, 1H), 8.24 (d, J=2.75 Hz, 2H), 10.35 (s,1H).

Synthesis of Structure 14:

Structure 13 (2.69 g, 8.1 mmol) was dissolved in MeOH (100 mL) and cooled to 0° C. NaBH$_4$ (460 mg, 12.2 mmol) was added and the reaction mixture was stirred at 0° C. for 1 hr. The reaction mixture was partitioned between brine (100 mL) and EtOAc (100 mL) and the organic layer was removed. The aqueous layer was extracted again with EtOAc (100 mL) and the combined organic phase was dried with Na$_2$SO$_4$, filtered and evaporated. The product was wet so the residue was again partitioned between brine (100 mL) and EtOAc (100 mL). The organic phase was then dried with Na$_2$SO$_4$, filtered and evaporated to give structure 14 (2.5 g, 92% yield) as a brown oil. $^1$H NMR (400 MHz, CDCl$_3$) δ 7.98 (d, J=2.56 Hz, 1H), 7.73 (d, J=2.56 Hz, 1H), 5.44 (s, 2H), 5.10 (s, 2H), 4.65 (s, 2H), 3.60 (s, 3H), 3.55 (s, 3H); $^{13}$C NMR (100 MHz, CDCl$_3$) δ 163.6, 155.8, 138.6, 136.9, 133.7, 125.4, 117.1, 101.5, 91.3, 60.0, 57.9, 57.6, 14.1.

Synthesis of Structure 15:

To a stirred solution of PPh$_3$ (2.75 g, 10.5 mmol) in DCM (40 mL) at room temperature under a nitrogen atmosphere was added imidazole (713 mg, 10.5 mmol) then iodine (2.66 g, 10.5 mmol) and the reaction mixture was stirred for 20 min. Structure 14 (2.5 g, 7.49 mmol) in DCM (20 mL) was then added and stirring continued for 1 hr at room temperature. The reaction mixture was concentrated in vaccuo (to approximately 20 mL) and the residue purified on silica with 40-60 petroleum ether:ethyl acetate (6:1) to give structure 15 (1.95 g, 59% yield) as a light yellow oil. $^{13}$C NMR (100 MHz, CDCl$_3$) δ 163.7, 155.1, 137.6, 137.0, 126.7, 116.8, 101.5, 91.6, 58.2, 58.1, −2.03.

Synthesis of Structure 16:

To a suspension of KH (176 mg, 4.39 mmol) in THF (20 mL) at 0° C. under a nitrogen atmosphere was added a solution of 4-tert-butylphenol (659 mg, 4.39 mmol) in THF (20 mL) and the mixture stirred for 15 min. A solution of structure 15 (1.95 g, 4.39 mmol) in THF (20 mL) was added to the reaction mixture, then it was warmed to room temperature and stirring continued for 16 hrs. The reaction was quenched with brine (100 mL) and extracted with EtOAc (2×100 mL). The combined organic phase was dried with Synthesis of Structure 12:

5-Bromosalicylic acid (6.5 g, 30 mmol) was dissolved in TFA (60 mL) and hexamethylenetetramine (20 g, 141 mmol) was added at room temperature. The reaction was warmed to 90° C. and stirred overnight (16 hrs). The solution was then poured into dilute hydrochloric acid (1 M, 200 mL), stirred Na$_2$SO$_4$, filtered and evaporated. The residue was lyophilised from MeCN:water (9:1) to give structure 16 (1.9 g, 93% yield) as a yellow oil. $^1$H NMR (400 MHz, CDCl$_3$), 7.96 (d, J=2.56 Hz, 1H), 7.86 (d, J=2.56 Hz, 1H), 7.32 (dd, J=6.87, 1.92 Hz, 2H), 6.91 (dd, J=6.86, 1.97 Hz, 2H), 5.45 (s, 2H), 5.19 (s, 2H), 5.11 (s, 2H), 3.55 (s, 6H), 1.30 (s, 9H).

Synthesis of Structure 17 (Ar=4-methoxyphenyl):

A solution of Pd(PPh$_3$)$_4$ (6.0 mg, 0.005 mmol) in degassed DMF (1.5 mL) was added to a mixture of structure 16 (60 mg, 0.13 mmol) and 4-methoxybenzeneboronic acid (21.52 mg, 0.14 mmol). A solution of Na$_2$CO$_3$ (66 mg, 0.62 mmol) in water (0.25 mL) was added and the reaction mixture was heated at 90° C. overnight. The residue was then partitioned between EtOAc (20 mL) and brine (20 mL). The organic phase was dried with Na$_2$SO$_4$, then filtered and evaporated. The residue was lyophilised in MeCN:H$_2$O (9:1) and then purified on silica with 40-60 petroleum ether:ethyl acetate (10:1) to give structure 17 (Ar=4-methoxyphenyl) (13 mg, 20% yield) as a yellow oil. ESMS= 495.4 [M+H]$^+$, 512.4 [M+NH$_4$]$^+$.

Synthesis of Structure 18 (Ar=4-methoxyphenyl):

Structure 17 (13 mg, 0.026 mmol) was dissolved in a solution of MeOH:concentrated HCl (99:1, 2 mL) and heated to 55° C. for 4 hrs. The reaction mixture was then diluted with MeCN:H$_2$O (9:1) and lyophilised to yield structure 18 (Ar=4-methoxyphenyl) (3.6 mg, 30% yield) as an off white powder. $^1$H NMR (400 MHz, CDCl$_3$) δ 1.30 (s, 9H), 3.84 (s, 3H), 5.20 (s, 2H), 6.97 (dd, J=2.44, 8.89 Hz, 4H), 7.32 (d, J=8.79 Hz, 2H), 4.47 (d, J=8.79 Hz, 2H), 7.94 (d, J=2.34 Hz, 1H), 8.06 (d, J=2.54 Hz, 1H) 10.75 (brs, 1H); LC/MS 407.1 [M+H]$^+$, 813.5 [2M+H]$^+$.

D. General Synthesis of 3-Aryloxymethyl Analogs of 5-Halo Salicyclic Acid

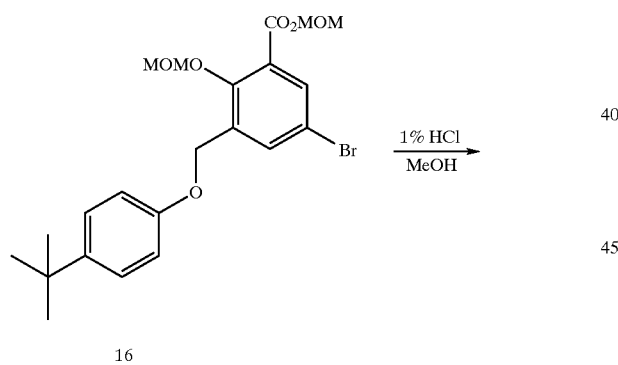

Synthesis of Structure 19:

Structure 16 (50 mg, 0.11 mmol) was dissolved in a solution of HCl:MeOH (99:1, 2 mL) and heated to 55° C. for 4 hrs. The reaction mixture was then diluted with MeCN:H$_2$O (9:1) and lyophilised to yield structure 19 (25.1 mg, 62%) as an off-white powder. $^1$H NMR (400 MHz, CDCl$_3$) δ 1.30 (s, 9H), 5.10 (s, 2H), 6.94 (d, J=8.60 Hz, 2H), 7.33 (d, J=8.60 Hz, 2H), 7.86 (d, J=1.64 Hz, 1H), 7.99 (d, J=2.38 Hz, 1H), 10.64 (brs, 1H); LC/MS 379.3 [M+H]$^+$.

E. General Synthesis of 3-Biaryloxymethyl Analogs of 5-Methyl Salicyclic Acid

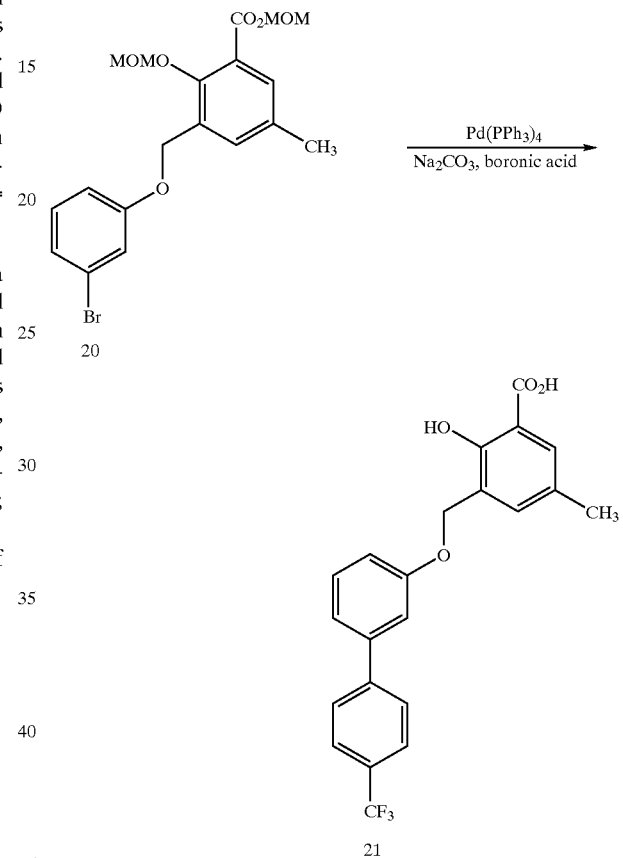

Synthesis of Structure 21:

A solution of Pd(PPh$_3$)$_4$ (11.0 mg, 0.01 mmol) in degassed DMF (2.0 mL) was added to a mixture of structure 20 (100 mg, 0.24 mmol) and 4-trifluorobenzeneboronic acid (49.1 mg, 0.26 mmol). A solution of Na$_2$CO$_3$ (100 mg, 0.94 mmol) in water (0.38 mL) was added and the reaction mixture was heated to 90° C. overnight. The residue was lyophilised from MeCN:H$_2$O (9:1) and purified on silica with EtOAc/40-60 petroleum ether (6.6:1) containing ACOH (1%) to give structure 21 (10.1 mg, 11% yield) as an off white solid. $^1$H NMR (400 MHz, CDCl$_3$) δ 2.31 (s, 3H), 5.20 (s, 2H), 7.06 (dd, J=2.87, 7.96 Hz, 1H), 7.19–7.21 (m, 1H), 7.26–7.27 (m, 1H), 7.36–7.38 (m, 1H), 7.52 (d, J=1.83 Hz, 1H), 7.66–7.71 9 m, 5H), 11.28 (brs,1H); LC/MS $t_R$=10.81 (403.3 [M+H]$^+$, 805.1 [M+H]$^+$.

Example 2
Representative Compounds of Structure (I)
TABLE 2
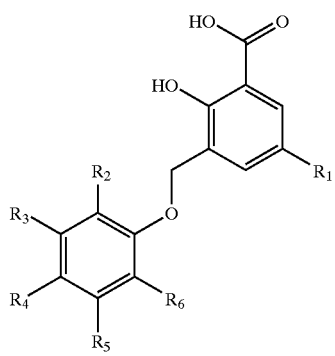
(I)
| Cpd. | R₁ | R₂ | R₃ | R₄ | R₅ | R₆ |
|---|---|---|---|---|---|---|
| 1 | —CH₃ | —C(CH₃)₃ | —H | —H | —H | —C(CH₃)₃ |
| 2 | —CH₃ | —H | —H | —C(=O)C₆H₅ | —H | —H |
| 3 | —CH₃ | —H | —H | —C(CH₃)₃ | —H | —H |
| 4 | —CH₃ | —H | —H | —Cl | —H | —H |
| 5 | —CH₃ | —H | —H | —H | —Cl | —Cl |
| 6 | —CH₃ | —H | —H | —OCH₂C₆H₅ | —H | —H |
| 7 | —CH₃ | —H | —H | —C(CH₃)₂CH₂CH₃ | —H | —H |
| 8 | —CH₃ | —H | —H | —C₆H₅ | —H | —H |
| 9 | —CH₃ | —H | —H | —H | —Cl | —H |
| 10 | —CH₃ | —H | —H | —C₆H₄-OCH₃ | —H | —H |
| 11 | —CH₃ | —H | —H | —H | —C(CH₃)₃ | —H |
| 12 | —CH₃ | —H | —H | —H | —H | —C₆H₅ |
| 13 | —CH₃ | —H | —H | —C(CH₃)₂CH₂C(CH₃)₃ | —H | —H |
| 14 | —C(CH₃)₂CH₂C(CH₃)₃ | —H | —H | —H | —H | —H |
| 15 | —C(CH₃)₂CH₂C(CH₃)₃ | —H | —H | —Br | —H | —H |

TABLE 2-continued

| # | Col1 | Col2 | Col3 | Col4 | Col5 | Col6 |
|---|---|---|---|---|---|---|
| 16 | neopentyl-like (2,4,4-trimethylpentan-2-yl) | —H | —H | —H | —H | —OCH₂CH₃ |
| 17 | —CH₃ | —H | —H | (cyclopentane-fused, positions 4,5) | | —H |
| 18 | —CH₃ | —H | —H | (cyclopentane-fused, positions 4,5) | | methyl 2-hydroxy-3-methyl-benzoate substituent |
| 19 | —CH₃ | —C(CH₃)₃ | —H | —CH₃ | —H | —C(CH₃)₃ |
| 20 | —CH₃ | —H | —H | —CH₃ | —H | —H |
| 21 | 2,4,4-trimethylpentan-2-yl | —H | —H | —CH(—)C(O)OCH₃ | —H | —H |
| 22 | 2,4,4-trimethylpentan-2-yl | —CH(—)OCH₃ | —H | —C(O)NH₂ | —H | —OCH₃ |
| 23 | 2,4,4-trimethylpentan-2-yl | —H | —H | —H | —H | —CH₂OH |
| 24 | 2,4,4-trimethylpentan-2-yl | —H | —H | —H | —H | benzothiazol-2-yl |
| 25 | —CH₃ | —H | —C(CH₃)₃ | 2-hydroxy-5-methylbenzoic acid via —OCH₂— | —H | —C(CH₃)₃ |
| 26 | —CH₃ | —H | —H | —H | —H | —C(CH₃)₃ |
| 27 | —H | —H | —H | —H | —H | benzothiazol-2-yl |
| 28 | —H | —H | —H | —C(CH₃)₂CH₂CH₃ | —H | —H |

TABLE 2-continued
| | | | | | | |
|---|---|---|---|---|---|---|
| 29 | —H | —H | —H | —H | —H | 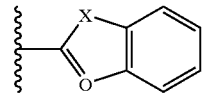 |
| 30 | —CH$_3$ | —H | —H | —Br | —H | —H |
| 31 | —CH$_3$ | —H | —H | —Cl | —H | —CH$_3$ |
| 32 | —CH$_3$ | —H | —H | 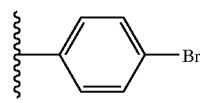 | —H | —H |
| 33 | —CH$_3$ | —H | —H | 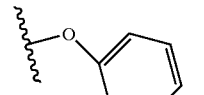 | —H | —H |
| 34 | —CH$_3$ | —H | —H | 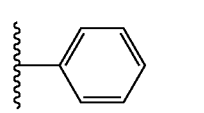 | —H | —H |
| 35 | —CH$_3$ | —H | —H | —I | —H | —H |
| 36 | —CH$_3$ | —H | —H | —H | —I | —H |
| 37 | —CH$_3$ | —H | —H | —CH$_2$CH$_3$ | —H | —H |
| 38 | —CH$_3$ | —H | —CH$_3$ | —H | —CH$_3$ | —CH$_3$ |
| 39 | —CH$_3$ | —H | —H | —H | 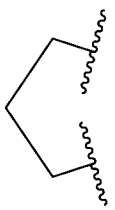 | |
| 40 | —CH$_3$ | —H | —H | —H | —H | —I |
| 41 | —CH$_3$ | —H | —H | —H | —Br | —H |
| 42 | —CH$_3$ | —H | —CH$_3$ | —H | —H | —F |
| 43 | —CH$_3$ | —H | —H | —Cl | —H | —Cl |
| 44 | 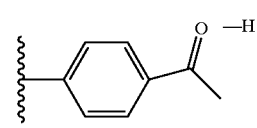 | —H | —H | —C(CH$_3$)$_3$ | —H | —H |
| 45 | 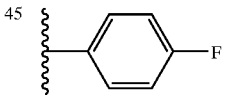 | —H | —H | —C(CH$_3$)$_3$ | —H | —H |
| 46 | 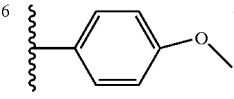 | —H | —H | —C(CH$_3$)$_3$ | —H | —H |
| 47 | 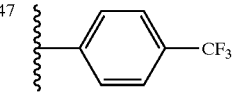 | —H | —H | —C(CH$_3$)$_3$ | —H | —H |
| 48 | 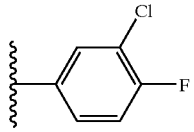 | —H | —H | —C(CH$_3$)$_3$ | —H | —H |

TABLE 2-continued

| # | R1 | | | R2 | | |
|---|---|---|---|---|---|---|
| 49 | benzofuran-2-yl | —H | —H | —C(CH₃)₃ | —H | —H |
| 50 | benzothiophen-2-yl | —H | —H | —C(CH₃)₃ | —H | —H |
| 51 | 3,5-difluorophenyl | —H | —H | —C(CH₃)₃ | —H | —H |
| 52 | 3-(trifluoromethyl)phenyl | —H | —H | —C(CH₃)₃ | —H | —H |
| 53 | thiophen-3-yl | —H | —H | —C(CH₃)₃ | —H | —H |
| 54 | thiophen-2-yl | —H | —H | —C(CH₃)₃ | —H | —H |
| 55 | —CH₃ | —H | —H | —H | thiophen-2-yl | —H |
| 56 | —CH₃ | —H | —H | —H | 4-methoxyphenyl | —H |
| 57 | —CH₃ | —H | —H | —H | 4-(trifluoromethyl)phenyl | —H |
| 58 | —CH₃ | —H | —H | —H | benzothiophen-2-yl | —H |
| 59 | —CH₃ | —H | —H | —H | benzofuran-2-yl | —H |
| 60 | —CH₃ | —H | —H | thiophen-2-yl | —H | —H |
| 61 | —CH₃ | —H | —H | 4-methoxyphenyl | —H | —H |

TABLE 2-continued

| # | | | | | | |
|---|---|---|---|---|---|---|
| 62 | —$CH_3$ | —H | —H | [benzofuran-2-yl] | —H | —H |
| 63 | —Br | —H | —H | —$C(CH_3)_3$ | —H | —H |
| 64 | —$CH_3$ | —H | —H | —H | [2-formylphenyl] | —H |
| 65 | —$CH_3$ | —H | —H | —H | [3,5-bis(CF$_3$)phenyl] | —H |
| 66 | —$CH_3$ | —H | —H | —H | [3-nitrophenyl] | —H |
| 67 | —$CH_3$ | —H | —H | —H | [4-isopropylphenyl] | —H |
| 68 | —$CH_3$ | —H | —H | —H | [furan-2-yl] | —H |
| 69 | —$CH_3$ | —H | —H | [4-isopropylphenyl] | —H | —H |
| 70 | —$CH_3$ | —H | —Cl | —Cl | —H | —Cl |
| 71 | —$CH_3$ | —H | —H | —H | —$CF_3$ | —H |
| 72 | —H | —H | —H | —$C(CH_3)_3$ | —H | —H |
| 73 | —$CH_3$ | —H | —H | —$C(CH_3)_3$ | —H | —OH |

Example 3

ANT Ligand Binding Assay of Representative Compounds

A competitive binding assay measuring the ability of compounds 1–73 to bind to an ANT polypeptide was performed. A modification of the procedures set forth in U.S. Ser. No. 09/569,327 entitled "Production of Adenine Nucleotide Translocator (ANT), Novel ANT Ligands and Screening Assays Therefor" (incorporated herein by reference) was utilized. In brief, competitive binding assays were performed using purified mitochondria from mammalian tissue or from *T. ni* cells infected with a baculovirus expressing ANT protein. The mitochondria were incubated with 0.5 nm of a labeled atractyloside derivative (e.g., $^{125}$I-ATR) and 20 $\mu$M of the compound to be tested or a control compound. After incubation of the mitochondria preparation with the compound and the labeled ligand, the reaction is applied to filter paper, the filter paper washed to remove non-specific binding, then dried and the bound radioactivity determined via scintillation counting. Preferably, compounds of the present invention will displace 50% of the radioactive ligand. To this end, all of the compounds in Table 2 satisfy these criteria.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure:

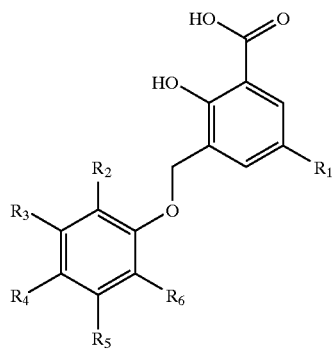

or a stereoisomer, prodrug or pharmaceutically acceptable salt thereof, wherein:

$R_1$ is hydrogen, halogen, nitro, cyano, alkyl, substituted alkyl, alkoxy, hydroxy, aryl, substituted aryl, —NHC(=O)R', heteroaryl or substituted heteroaryl;

$R_2$, $R_3$, $R_5$ and $R_6$ are the same or different and independently hydrogen, halogen, nitio, cyano, alkyl, substituted alkyl, alkoxy, hydroxy, aryl, substituted aryl, heteroaryl or substituted heteroaryl, $R_4$ is hydrogen, halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, —O—$R_7$, —C(=O)—$R_7$, —C(=O)O—$R_7$, —C(=O)—NH—$R_7$ or —NHC(=O)R";

$R_7$ is hydrogen, alkyl, substituted alkyl, aryl, substituted aryl, arylalkyl or substituted arylalkyl;

R' and R" are the same or different and independently alkyl, substituted alkyl, aryl, substituted aryl, heteroaryl or substituted heteroaryl; and $R_4$ and $R_5$ or $R_5$ and $R_6$, taken together with the carbon atoms to which they are attached, optionally form a substituted or unsubstituted homocycle, with the proviso that the compound is not 3,5-bis(p-tolyoxymethyl)salicylic acid.

2. The compound of claim 1 wherein $R_1$ is hydrogen.
3. The compound of claim 1 wherein $R_1$ is alkyl.
4. The compound of claim 3 wherein alkyl is methyl.
5. The compound of claim 3 wherein alkyl is —C(CH$_3$)$_2$—CH$_2$—C(CH$_3$)$_2$—CH$_3$.
6. The compound of claim 1 wherein $R_2$ is hydrogen.
7. The compound of claim 1 wherein $R_3$ is hydrogen.
8. The compound of claim 1 wherein $R_4$ is hydrogen.
9. The compound of claim 1 wherein $R_4$ is halogen.
10. The compound of claim 1 wherein $R_4$ is alkyl.
11. The compound of claim 10 wherein alkyl is tert-butyl.
12. The compound of claim 1 wherein $R_4$ is heteroaryl.
13. The compound of claim 12 wherein heteroaryl is thiophenyl.
14. The compound of claim 1 wherein $R_5$ is hydrogen.
15. The compound of claim 1 wherein $R_5$ is halogen.
16. The compound of claim 1 wherein $R_6$ is hydrogen.
17. The compound of claim 1 wherein $R_6$ is halogen.

18. A composition comprising a compound in combination with a pharmaceutically acceptable carrier, said compound having the following structure:

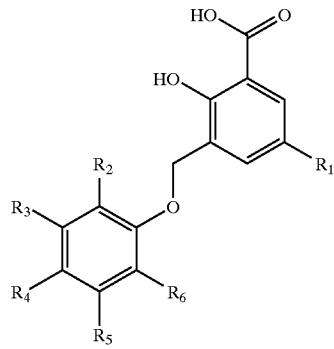

or a stereoisomer, prodrug or pharmaceutically acceptable salt thereof, wherein:

$R_1$ is hydrogen, halogen, nitro, cyano, alkyl, substituted alkyl, alkoxy, hydroxy, aryl, substituted aryl, —NHC(=O)R', heteroaryl or substituted heteroaryl;

$R_2$, $R_3$, $R_5$ and $R_6$ are the same or different and independently hydrogen, halogen, nitro, cyano, alkyl, substituted alkyl, alkoxy, hydroxy, aryl, substituted aryl, heteroaryl or substituted heteroaryl;

$R_4$ is hydrogen, halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, —O—$R_7$, —C(=O)—$R_7$, —C(=O)O—$R_7$, —C(=O)—NH—$R_7$ or —NHC(=O)R";

$R_7$ is hydrogen, alkyl, substituted alkyl, aryl, substituted aryl, arylalkyl or substituted arylalkyl;

R' and R" are the same or different and independently alkyl, substituted alkyl, aryl substituted aryl, heteroaryl or substituted heteroaryl; and $R_4$ and $R_5$ or $R_5$ and $R_6$, taken together with the carbon atoms to which they are attached, optionally form a substituted or unsubstituted homocycle.

19. A method for treating a condition in a mammal associated with altered mitochondrial function, comprising administering to a mammal in need thereof an effective amount of a composition of claim 18, wherein the condition is: Alzheimer's Disease; diabetes mellitus; obesity; Parkinson's Disease; Huntington's disease; dystonia; Leber's hereditary optic neuropathy; schizophrenia; mitochondrial encephalopathy, lactic acidosis, and stroke (MELAS); psoriasis; mitochondrial diabetes and deafness (MIDD); myoclonic epilepsy ragged red fiber syndrome; osteoarthritis; or Friedrich's ataxia.

20. The method of claim 19 wherein the condition is: Alzheimer's Disease; diabetes mellitus; obesity; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD); myoclonic epilepsy ragged red fiber syndrome; osteoarthritis; or Friedrich's ataxia.

* * * * *

UNITED STATES PATENT AND TRADEMARK OFFICE
CERTIFICATE OF CORRECTION

PATENT NO. : 6,936,638 B2
DATED : August 30, 2005
INVENTOR(S) : Soumitra S. Ghosh et al.

It is certified that error appears in the above-identified patent and that said Letters Patent is hereby corrected as shown below:

Column 31,
Line 45, "tolyoxymethyl" should read as -- tolyloxymethyl --.

Column 32,
Lines 54-61, claim 20 should have been cancelled.

Signed and Sealed this

Twenty-ninth Day of November, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,936,638 B2 |
| APPLICATION NO. | : 10/741595 |
| DATED | : August 30, 2005 |
| INVENTOR(S) | : Soumitra S. Ghosh et al. |

It is certified that error appears in the above-identified patent and that said Letters Patent is hereby corrected as shown below:

On the title page, Item (75) Inventors, 4th Inventor should read -- Sprios Liras --

Signed and Sealed this

Fourth Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,936,638 B2 | |
| APPLICATION NO. | : 10/741595 | |
| DATED | : August 30, 2005 | |
| INVENTOR(S) | : Soumitra S. Ghosh et al. | |

It is certified that error appears in the above-identified patent and that said Letters Patent is hereby corrected as shown below:

On the title page, Item (75) Inventors, -- Spiros Liras -- should replace "Spiros J. Liras".

Signed and Sealed this

Eighteenth Day of September, 2007

JON W. DUDAS
*Director of the United States Patent and Trademark Office*